US007306584B2

(12) United States Patent
Wessman et al.

(10) Patent No.: US 7,306,584 B2
(45) Date of Patent: Dec. 11, 2007

(54) METHOD AND ARRANGEMENTS IN ASEPTIC PREPARATION

(75) Inventors: Göran Wessman, Göteborg (SE); Kjell Andreasson, Västra Frölunda (SE)

(73) Assignee: Carmel Pharma AB, Göteborg (SE)

( * ) Notice: Subject to any disclaimer, the term of this patent is extended or adjusted under 35 U.S.C. 154(b) by 685 days.

(21) Appl. No.: 10/344,095

(22) PCT Filed: Aug. 9, 2001

(86) PCT No.: PCT/SE01/01726

§ 371 (c)(1),
(2), (4) Date: Feb. 10, 2003

(87) PCT Pub. No.: WO02/11794

PCT Pub. Date: Feb. 14, 2002

(65) Prior Publication Data

US 2004/0215147 A1 Oct. 28, 2004

(30) Foreign Application Priority Data

Aug. 10, 2000 (SE) .................................... 0002868

(51) Int. Cl.
*A61M 31/00* (2006.01)
(52) U.S. Cl. ...................................................... 604/500
(58) Field of Classification Search ................ 141/329, 141/18, 25–27; 604/190, 403–405, 93.01, 604/126, 122, 406, 129, 181, 533, 500, 506, 604/507
See application file for complete search history.

(56) References Cited

U.S. PATENT DOCUMENTS 4,137,917 A * 2/1979 Cohen ........................ 604/513
4,600,040 A * 7/1986 Naslund ...................... 141/18
4,768,568 A * 9/1988 Fournier et al. ............ 141/286
4,820,276 A 4/1989 Moreno
5,017,186 A 5/1991 Arnold
5,102,406 A * 4/1992 Arnold ....................... 604/405
5,334,163 A * 8/1994 Sinnett ....................... 604/236

FOREIGN PATENT DOCUMENTS

| | | |
|---|---|---|
| GB | 938777 | 9/1961 |
| WO | 9014798 | 12/1990 |
| WO | 0035517 | 6/2000 |

* cited by examiner

*Primary Examiner*—Nicholas D. Lucchesi
*Assistant Examiner*—Christopher D. Koharski
(74) *Attorney, Agent, or Firm*—Dykema Gossett PLLC

(57) ABSTRACT

A first aspect of the invention relates to a method for aseptic preparation with an injection syringe. The syringe comprises a container for injection agent and an immovable connection nozzle connected to the container. The method entails charging the container with air. According to the invention air is forced to pass through an air filter arranged on the connection nozzle. This enables the syringe container to be charged with aseptic air in a simple and reliable fashion. Other aspects of the invention relate to devices for performing the method, viz. an injection syringe equipped with an air filter in the connection nozzle, a filter unit (2) connectable to an injection syringe's (1) connection nozzle (13) and a system comprising an injection syringe (1) and a separate filter unit (2). The invention devices convey advantages of the same kind as the invention method.

5 Claims, 4 Drawing Sheets

METHOD AND ARRANGEMENTS IN ASEPTIC PREPARATION

The present application is a U.S. national phase of PCT/SE01/01726, filed 9 Aug. 2001, which claimed priority of Danish application No. 0002868-8, filed 10 Aug. 2000. All priorities are claimed.

FIELD OF THE INVENTION

A first aspect of the present invention relates to a method of aseptic preparation using an injection syringe. In addition, a second aspect of the invention relates to an injection syringe for aseptic preparation, a third aspect relates to a filter unit for an injection syringe, and a fourth aspect relates to a system for accomplishing the inventive method.

The method and the invention arrangements for performing the method therefore relate to aseptic preparation of an injection agent, such as a medication, for the purpose of achieving a solution for direct injection or injection through a tube connected to a patient. The invention can also be applied to sterile or aseptic handling of different liquids for use in medicine or diagnostics.

BACKGROUND OF THE INVENTION

Eliminating all sources of infection is extremely important when solutions of the aforementioned kind are prepared. Every stage in solution preparation must therefore be performed with the goal of eliminating the risk of contamination, thereby denying bacteria and other contaminants access to the solution being prepared.

Charging the syringe first with air is normally necessary when an injection syringe is to be filled with an injection agent. This is to expel air from the container from which the injection syringe is filled with injection agent to prevent the formation of any vacuum, which would impede filling, as the injection syringe fills. The air with which the syringe is charged is a potential source of contamination during preparation of an injection solution. Ordinary atmospheric air could contain different kinds of bacteria and other contaminants which might transfer to the injection solution and/or residual injection agent in the container unless special precautions are taken.

Injection syringes are therefore normally charged with air in special fume cupboards in which air is filtered before reaching the fume cupboard, thereby rendering the air aseptic, or air filling is performed in a sterile room. A relatively large investment is accordingly required at the liquid preparation site to ensure access to aseptic air. Many locations and situations have no access to fume cabinets or sterile rooms.

The provision of sterile air in a special container, from which air can be drawn for medication preparation, has therefore previously been proposed for the aseptic preparation of medication solutions.

Thus, U.S. Pat. No. 5,017,186 describes an apparatus comprising a container holding sterile compressed air and a vessel for use in the preparation of an injection drug. The use of means for connecting the container holding sterile air and the vessel makes it possible to transfer a charge of low-pressure sterile air from the container to the vessel. The vessel is equipped with means for sealing the container after the charge of sterile air has been received from the container. It also has walls, impermeable to air, and an opening which is sealed off with a punctionable, self-sealing membrane. According to U.S. Pat. No. 5,017,186, the walls of the vessel are essentially non-resilient and can be made of e.g. glass or acrylic plastic. The means for connecting the container holding sterile air and the vessel to be filled with sterile air consists of a coupling tailored to the kind of vessel to be filled, a pressure gauge and a valve. According to an alternative embodiment described in U.S. Pat. No. 5,017,186, a vessel containing sterile air and a bottle containing an injectable drug are provided in a tandem arrangement.

PCT/SE99/02144 describes a gas container for supplying aseptic air, the container having resilient walls.

Another example of aseptic air supplied in a container is provided in U.S. Pat. No. 5,102,406. The container is first charged with aseptic air which can be prepared at the fabrication site. When air is to be drawn into a syringe, the syringe needle penetrates a wall in the container and air is sucked into the syringe. The container is equipped with a wall filter through which filtered air can be replenished.

An injection syringe, equipped with a system of different filters for fluid filtration and a revolver-mounted connection channel for connecting the syringe cannula for fluid filtration, is also known from U.S. Pat. No. 4,820,276. The possibility of devising one of the filters as an air filter through which air can be drawn in is also cited as an option. As a result of its design, the syringe is rather complex and has interacting moving parts. Erroneous handling is also a risk since the connection channel could be connected to the wrong filter for a particular solution.

DESCRIPTION OF THE INVENTION

The objective of the present invention is to achieve a simple method and arrangements for aseptic filling of an injection syringe, with no need for special fume cupboards or sterile rooms, and to eliminate the need for special sterile air containers.

According to a first aspect of the invention, this objective is achieved with a method wherein air is sucked in directly from the atmosphere through an air filter arranged in connection to the injection syringe's container, the filter removing bacteria and other contaminants from the admitted air. Neither a sterile environment nor any special sterile air container is therefore necessary. Thus, the invention method makes it possible to fill an injection syringe just about anywhere and at very low cost. The method can be used with a very simple, standard syringe.

According to one preferred embodiment, a special filter unit can be arranged at the connection nozzle. The method can therefore be used with existing, standard syringes.

According to an alternative embodiment, the method can be used with an injection syringe which is already equipped with a connection nozzle fitted with an air filter. This would eliminate the need for additional accessories.

The communication between filter and container is suitably interrupted after the injection syringe has been charged with air, thereby facilitating subsequent stages in the process. This accordingly constitutes an additional, preferred embodiment of the invention method.

In a preferred embodiment, the interruption is accomplished by detaching the filter. This allows the use of a very simple filter.

In an alternative preferred embodiment, the interruption is accomplished by closing the communication between the container and the air filter and opening a communication between the container and a nozzle outlet. This simplifies the operation, since the filter need not to be detached before connecting the syringe to the vessel.

According to an additional preferred embodiment of the invented method, an airtight connection is established between the connection nozzle and a vessel containing the injection agent. Air in the injection syringe's injection agent container is then forced into the vessel, and injection agent flows from the vessel into the injection agent container. This represents a particularly useful application of the invention method.

According to one preferred embodiment, this connection is achieved with a separate coupling means. The use of such a coupling means reduces the risk of exposing preparation staff to injection agent leaking into atmosphere. This could be a serious problem in the preparation of cytostatics, i.e. drugs known to present an occupational hazard when released into atmosphere. Antiviral agents, antibiotics and radioactive drugs are other items capable of causing problems in the occupational environment.

According to another preferred embodiment of the invented method, a cannula on the coupling means is made to penetrate a membrane on the coupling means and a membrane on the vessel. This method establishes an airtight connection between the injection agent container and the vessel in a simple and reliable manner.

According to another preferred embodiment of the invented method, the vessel is made to undergo a change in volume after connection to the injection syringe. This thereby equalises pressure in the vessel when air is introduced into it and/or injection agent is withdrawn from it. This facilitates these steps in the preparation process.

According to another preferred embodiment of the invented method, a separate coupling means is attached to the connection nozzle such that during charging the container with air, air passes through the air filter into the coupling means and from the coupling means through the connection nozzle into the container, whereafter the coupling means is connected to a vessel containing the injection agent.

This eliminates the need to exchange the unit that is attached to the connection nozzle and thereby further decreases the risk for contamination.

Since the injection syringe is accordingly provided with an air filter arranged at its connection nozzle, a means is obtained whereby the invention method can be implemented in an expedient manner. No other component, apart from the injection syringe itself, is required to fill the syringe with aseptic air. The invention injection syringe conveys advantages of the same kind as the invention method, and air-filling can therefore be carried out with no need for a fume cupboard, sterile room or special clean air containers. The invented syringe also has a very simple design, thereby reducing e.g. the risk of erroneous handling.

According to a preferred embodiment of the syringe, the connection nozzle includes a valve, operable between a first position, in which communication is established between the container and the air filter, and a second position, in which said communication is closed, while communication between the container and a nozzle outlet is established. This embodiment allows connecting the syringe to a vessel without detaching the filter.

According to a third aspect of the invention, the objective is achieved when a filter unit is equipped with a connection device for connection to the connection nozzle on an injection syringe.

According to a preferred embodiment, the filter unit's connection device consists of the female part of a Luer connector or Luer-Lok connector. Since the injection syringe's connection nozzle is usually devised with a corresponding male part, the filter can also be used with most syringes on the market.

According to another preferred embodiment of the invented filter unit, the housing is provided with a valve, a first opening in the connection device, a second opening provided with the air filter and a third opening, the valve being operable between a first position, in which communication is established between the first and second openings, and a second position, in which said communication is closed and communication is established between the first and third openings. A filter unit according to this embodiment does not need to be detached before connecting the syringe to a vessel, which simplifies the operation.

According to a fourth aspect of the invention, the objective is achieved when the system primarily comprises an injection syringe and a filter unit with an air filter. Since the filter unit has a coupling means, making it possible to establish an airtight connection to the injection syringe's connection nozzle, components intended for direct connection with one another in performing the invention method in a simple and reliable fashion, become available. When these components are supplied as a complete system, the air filter and injection syringe are certain to fit together.

According to a preferred embodiment of the system, the system also comprises a coupling means as a separate unit with which an airtight connection can be established with the injection syringe's connection nozzle. This coupling means makes it possible to perform the invention method in a manner reducing the risk of leakage of injection agent into atmosphere. Advantages of the kind corresponding to those cited above for the preferred embodiments of the invention method are thereby achieved. One such system could alternately comprise an injection syringe incorporating an integrated filter instead of a separate syringe and filter.

According to an additional preferred embodiment of the invented system, the system also includes a coupling means, attachable to the invention syringe with an airtight connection. This results in a complete system with components which fit each other and which ensure the provision of both aseptic air and risk-free handling of injection agent.

According to another preferred embodiment of the invented system, the injection agent vessel is provided with a pressure-equalisation device which facilitates the expelling of air and aspiration of injection agent.

According to another preferred embodiment of the invented system, the injection agent vessel is equipped with a first membrane, coupling means with a second membrane and a cannula, the cannula being arranged to penetrate both membranes when the injection means vessel is connected to the coupling means. This version is a simple, safe and practical arrangement for ensuring that the air is not contaminated by atmosphere and that injection agent does not leak into atmosphere.

According to another preferred embodiment of the invented system, the coupling means comprises a connection arrangement capable of airtight connection to the separate filter unit. This allows the air to be aspirated to the container without exchanging the unit that is attached to the connection nozzle and thereby further decreases the risk for contamination.

The coupling means and the injection agent vessel connectable to same, as cited in the preceding embodiments, are components which are in themselves prior art. They are described in e.g. the aforementioned PCT/SE99/02144. However, the advantages achieved with this application's system for achieving aseptic air are particularly valuable when the system is employed in a system which also comprises the cited components, as a holistic solution, providing maximal safety in different respects in all the steps in the preparation process, is thereby achieved The invention will be explained in greater detail below in descriptions of the preferred embodiments and referring to attached drawings.

DESCRIPTION OF THE EMBODIMENTS

Figure 1:
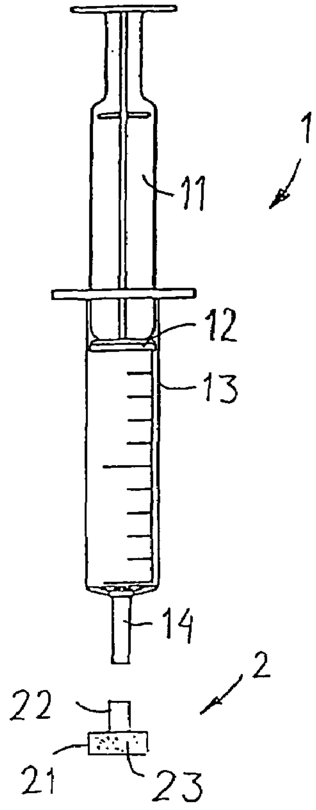
FIG. 1 is a lateral view of a system comprising an injection syringe and a filter unit according to a first embodiment of the invention.

FIG. 1 shows a conventional injection syringe 1 with a piston rod 11, piston 12 and injection agent container 13 and a connection nozzle 14. A filter unit 2, consisting of a housing 21, a connection arrangement 22 and an air filter 23, are also shown. The air filter 23 is suitably a HEPA filter so even very tiny particles are filtered out in it.

The injection syringe's 1 connection nozzle 14 is devised as a Luer connector and is therefore slightly tapered. In the corresponding manner, the filter unit's 2 connection arrangement 22 is provided with an internally tapered channel and constitutes the female part of a Luer connector. The filter unit 2 can thereby be connected to the injection syringe's connection nozzle 14.

Figure 2:
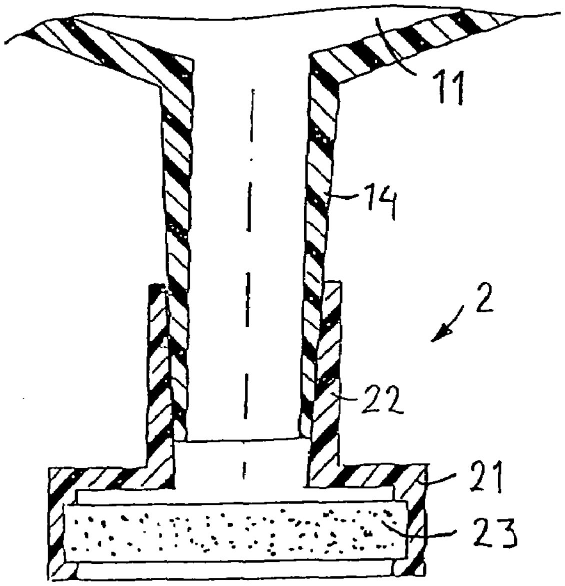
FIG. 2 is an enlarged section of the system in FIG. 1 with the components interconnected.
Figure 1A:
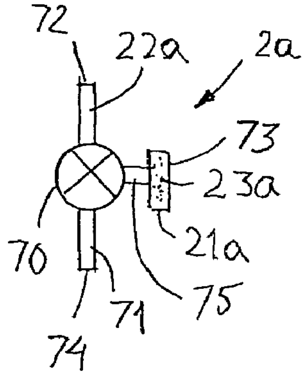
FIG. 1*a* is a lateral view of a filter unit according to an alternative example.

FIG. 2 shows an enlarged view of the filter unit 22 connected to the injection syringe's 1 connection nozzle 14.

FIG. **1*a* shows another example of the filter unit 2*a*. The filter unit 2*a* has a connection device 22*a* for connection to the nozzle 14 of the syringe 1 shown in FIG. 1. The connection device 22*a* has an opening 72 and is similar to that of the filter unit 2 shown in FIGS. 1 and 2. The filter unit has also a connection arrangement 71 with an opening 74 provided for a connection to an injection agent vessel 4 of the type shown in FIG. 4. The filter unit also has a branch connection 75 to an air filter 23*a* in a housing 21*a* provided with an opening 73. A valve 70 is provided in the filter unit 2*a*. The valve 70, in a first position, establishes communication between openings 72 and 73, whereas the opening 74 is cut off from communication with the other openings. In a second position, the valve 70 establishes communication between the openings 72 and 74, whereas the opening 73** is cut off from communication with the other openings.

When using the filter unit according to FIG. **1*a*, the unit can be maintained connected to the syringe, when it is connected to the injection agent vessel 4 for performing the operation illustrated in FIGS. 7-13**.

When an injection solution is prepared, the injection syringe is first charged with air. The piston 12 is then pressed to the bottom of the injection agent container 13 and then retracted. As it moves upward, air is drawn into the injection agent container 13, filling this container with air when piston travel is completed. During air intake, the filter unit 2 is attached to the syringe's connection nozzle 14 as shown in FIG. 2. Admitted air is then forced through the air filter 23 in the filter unit 2, causing the injection agent container 13 to fill with aseptic air.

Once the syringe's injection agent container 13 is charged with air, the syringe is ready for filling with an injection agent. The filter unit 2 is then removed, and the syringe's connection nozzle 14 is connected to a vessel containing the injection agent to be administered. Aseptic air is forced into the vessel, whereupon injection agent is drawn into the syringe's injection agent container. This is conventional procedure and does not require any detailed explanation.

Figure 3:
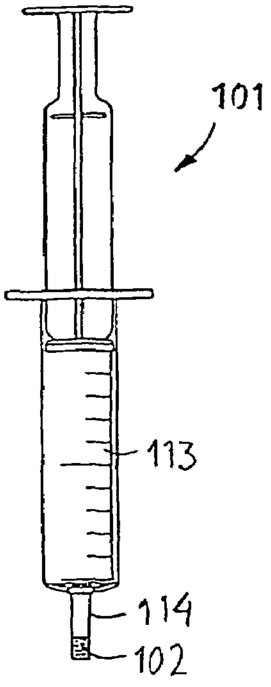
FIG. 3 is a lateral view of an injection syringe according to an alternative embodiment of the invention.

FIG. 3 illustrates a second embodiment of an injection syringe 101. In this embodiment, the syringe has a special design in which a filter 102 is pre-mounted on the syringe's connection nozzle 114. The same procedure as is described for FIG. 1 is used for drawing in air.

The syringe 101 shown in FIG. 3 can alternatively have a nozzle provided with a filter of a construction corresponding to that of the filter unit shown in FIG. **1*a***.

Figure 4:
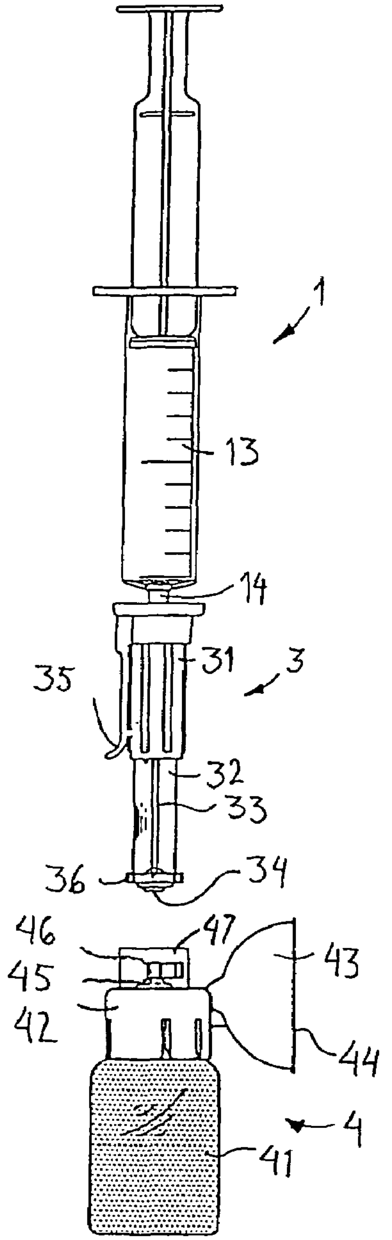
FIG. 4 is a lateral view of a system according to a second embodiment of the invention, the said system comprising additional components.

The components illustrated in FIGS. 1 and 2, i.e. an injection syringe 1 and a filter unit 2, can advantageously constitute a system of components provided in a single context. FIG. 4 illustrates an embodiment in which the system comprises a coupling means 3 and an injection agent vessel 4, in addition to the components shown in FIGS. 1 and 2.

Figure 5:
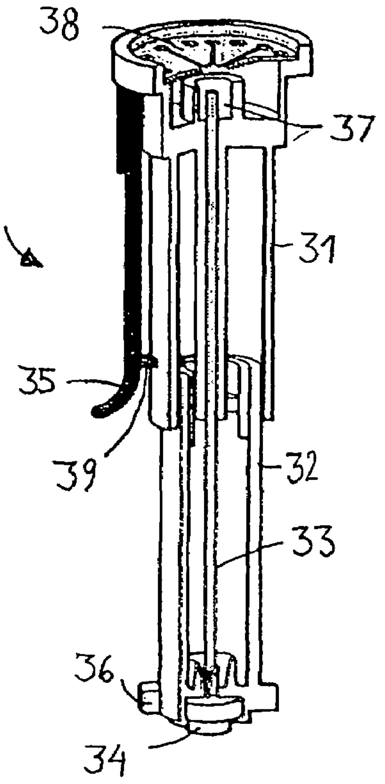
FIG. 5 is a cut-away view of a first component in the system in FIG. 4.

The coupling means 3 is shown in greater detail in FIG. 5 which is a cutaway view. The coupling means consists of a first part 31, arranged for connection to the syringe 1, and a second part 32, arranged for connection to the injection agent vessel 4. The second part 32 can be telescoped into the first part 31. In the position shown in FIG. 5, this is prevented by a detent 39 which slips into an opening in the first part 31, thereby preventing the second part from rising. This locked position can be released with a handle 35 connected to the detent 39 and attached to the upper end of the first part 31. The handle is pulled outward with a finger against the resilient force of its own resistance to bending.

The first part 31 is equipped with the female part 37 of a Luer connector with which the first part is connected to the injection syringe's 1 connection nozzle 14. The latter is guided into place by metal tongues 38 arranged next to the Luer connector 37. A cannula 33, shown in the fig. with its tip pointing down, is arranged in the coupling means 3. At the bottom of the fig., the coupling means 3 is sealed with a membrane 34 and provided with flanges 36 for bayonet connection to the injection agent vessel 4. In the depicted position, the cannula 33 is protected inside the coupling means 3. Pressing the first section 31 and the second section 32 of the coupling means 3 together forces the cannula 33 downward to penetrate the membrane 34.

The injection agent vessel shown in FIG. 4 consists of a bottle 41 with a capping means 42 providing airtight sealing of the bottle. The capping means 42 has a collar 47 provided with slits 46 arranged to interact with the connection flanges 36 on the coupling means 3. The capping means 42 is additionally provided with a pressure-equalisation chamber 43 whose volume can vary because one wall consists of an elastic film 44. The capping means 42 also has a membrane 45 located inside the collar 47.

Figure 6:
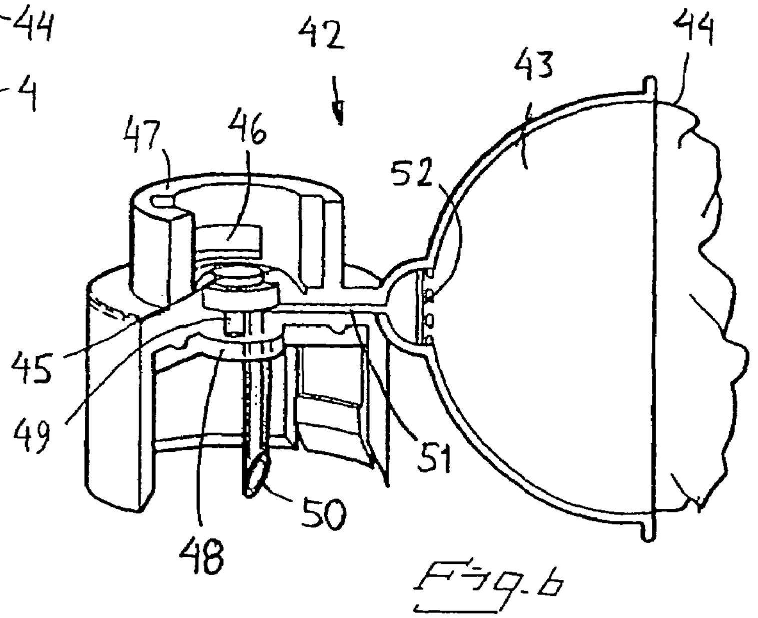
FIG. 6 is a cut-away view of a detail in a second component in the system in FIG. 5.
Figure 7:
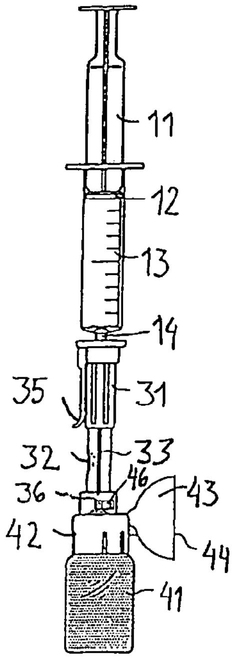
FIGS. 7-13 illustrate different stages in use of the system shown in FIG. 4.

The capping means 42 is shown in greater detail in a cut-away view in FIG. 6. It is equipped with a lid section 48. A channel 49, extending to the membrane 45 and covered by it, passes through the lid section. The bottle (not shown in FIG. 6) is connected to the pressure equalisation chamber 43, via a filter 52, by means of an air channel 50 and a connecting channel 51. Changes in pressure are accommodated by the bulging or depression of the film 44.

The way in which the components cited in FIGS. 4-6 interact and the procedure for their handling will henceforth be described with reference to FIGS. 7-13.

The syringe is ready to be charged with injection agent from a vessel 4 once the injection syringe 1 is charged with aseptic air, as described in conjunction with FIGS. 1-3, and the coupling means 3 has been attached to the injection syringe's 1 connection nozzle 14, as illustrated in FIG. 4.

The lower end of the capping means 3 is then connected to the vessel's capping means 42 by means of the Luer connector's bayonet mount 36, 46.

Figure 8:
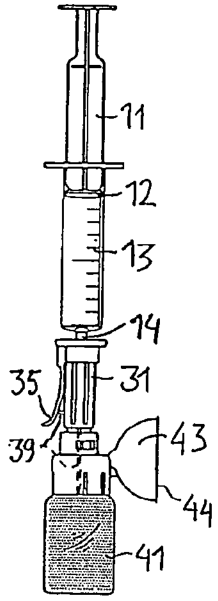

FIG. 8 illustrates the next step. The detent 39 is released from the locking position when the control handle 35 is moved outwards. Both parts of the coupling means 31, 32 are then pressed together as described for FIG. 5, the position shown in FIG. 8 then being assumed. The cannula 33 of the coupling means 3 then penetrates the membranes 34, 35 on the coupling means 3 and vessel's coupling means 42 respectively, thereby opening a connection between the injection syringe's container 13 and the bottle 41.

Figure 9:
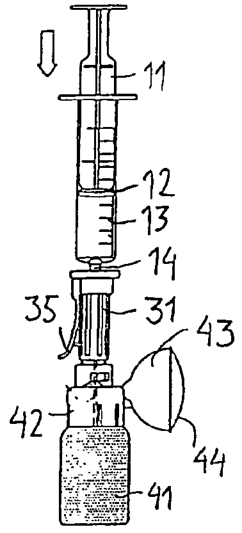

In the next step, shown in FIG. 9, the injection syringe's 12 piston is depressed, leading to the expulsion of air from the container 13 through the coupling unit 3 and cannula 33 into the bottle 41 containing the injection agent. The rise in pressure is accommodated by the channel connection 50, 51 and the pressure equalisation chamber 43, described for FIG. 6, the positive pressure causing the film 44 to bulge.

Figure 10:
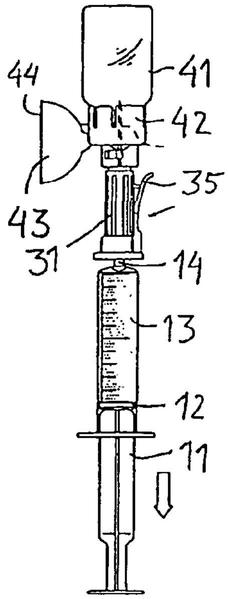
Figure 11:
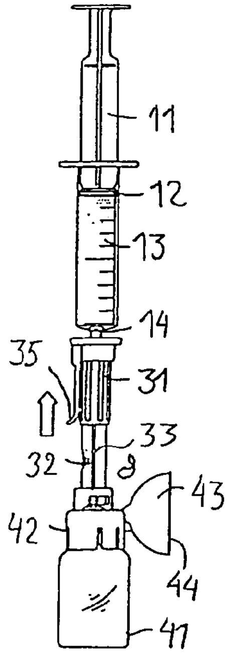

The entire system is then turned upside down, as shown in FIG. 10, and injection agent is drawn into the injection syringe's 1 container 13 when the piston 12 is retracted. The system is then returned to its original position. The parts 31, 32 of the coupling means are separated, as shown in FIG. 11, and the detent 39 returns to the locked position.

Figure 12:
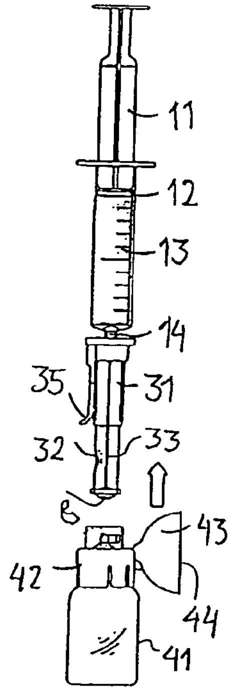

FIG. 12 shows the way in which the injection agent vessel 4 is subsequently detached from the coupling means 3 by rotating the bayonet mount 36, 46. The injection syringe 1 has now been charged with injection agent and is ready for use.

Figure 13:
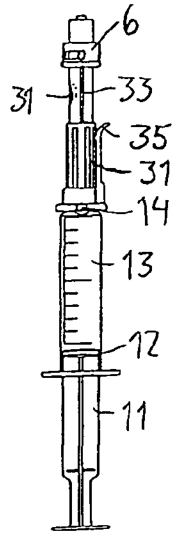

In those instances in which injection agent is to be administered to a patient through an injection line connected to the patient, the system also comprises an adapter unit 6 which is attached to the coupling unit 3 with a bayonet mount, as shown in FIG. 13.

Figure 14:
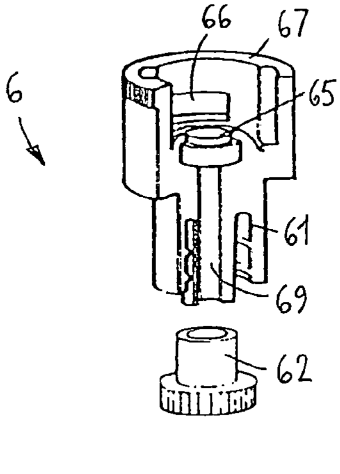
FIG. 14 is a cut-away view of a component shown in FIG. 13.

The adapter unit 6 is shown in greater detail in a cut-away view in FIG. 14. It is fitted with a collar 67 with slits 66 which, in the same way as the corresponding parts on the vessel's 4 coupling means 42, mates with the connection flanges on the coupling means 3 in connection. The adapter unit 6 has a membrane 65 which, when the unit is connected to the coupling means 3, presses against the coupling means membrane 34.

The opposite end of the adapter means 6 is fitted with a Luer-Lok connector 61 for connection with a connection unit on the patient's injection line. When the agent is to be injected, the parts 31, 32 of the coupling means are pressed together in the same way as described above, causing the cannula 33 to penetrate the two membranes 34 and 65 and establishing a connection between the injection syringe's container 13 and the injection line. A protective means 62 can be detachably attached to the adapter 6 during transportation etc.

Figure 15:
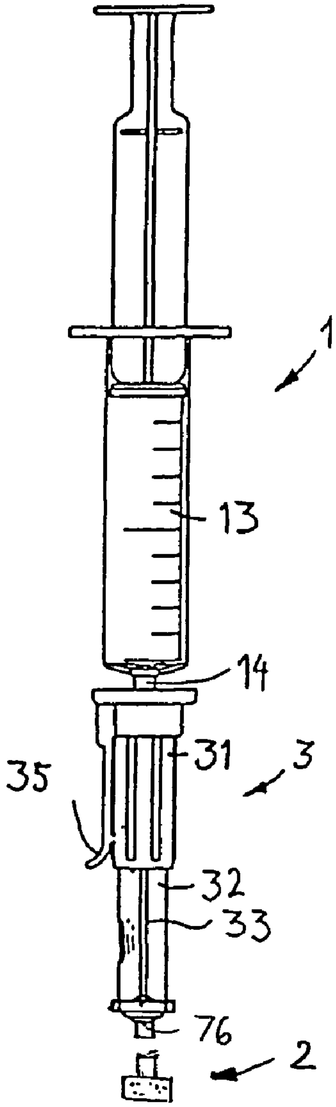
FIG. 15 is a lateral view of a further embodiment of the invention.

FIG. 15 illustrates an alternative example how to perform the invented method. In this case the coupling means 3 illustrated in FIG. 4 is attached to the connection nozzle 14 of the syringe 1 during the charging of air. The filter unit 2 is attached to the other end of the coupling means 3, which is provided with a male-part 76 of a Luer connector. When the charging of air is finished, the filter unit 2 is removed and the coupling means is connected to an injection agent vessel 4 as described in connection with FIG. 4. FIG. 15 is intended to illustrate the principle of locating the filter at the lower end of the coupling means 3. In practice it can be realized by providing an adapter unit that is similar to the adapter unit 6 of FIG. 14 having a filter unit fixedly attached to its lower end, e.g. a unit corresponding to detail 62 of FIG. 14.

Figure 16:
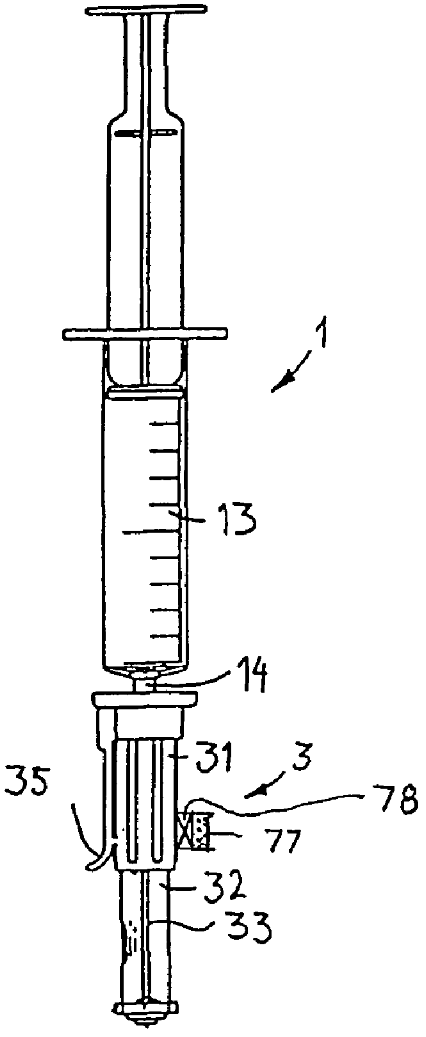
FIG. 16 is a lateral view of yet a further embodiment of the invention.

A further alternative example is illustrated in FIG. 16. In this embodiment the coupling means 3 has a branch connection including an air filter 77 and a shut-off valve 78. During charging with air, the valve 78 is open and air is aspired through the filter 77 into the coupling means 3 and further to the container 13 of the syringe 1. When the charging is finished, the valve 78 is closed and the coupling means is connected to the injection agent vessel. For practical reasons it might be advantageous to attach the filter 77 at the end of the coupling means facing the syringe 1.

The invention claimed is:

1. A method for antiseptic preparation by means of a liquid injection syringe, said liquid injection syringe comprising a container for a liquid injection agent and an immovable connection nozzle attached to the container, the method including the sequential steps of:

mounting an air filter on the connection nozzle, charging the container with air, removing the air filter from the connection nozzle, connecting the connection nozzle to a vessel containing a liquid injection agent via a separate coupling means to provide an air-tight connection between the connection nozzle and the vessel, forcing the air from the container into the vessel, and thereafter, while the connection nozzle is maintained connected to the vessel, drawing liquid injection agent from the vessel into the container, wherein charging the container with air causes air to pass through the connection nozzle and the air filter mounted on the connection nozzle.

2. The method according to claim 1, wherein a separate filter unit is attached to the connection nozzle before the container is charged with air.

3. The method according to claim 1, wherein a cannula of the coupling means is forced to penetrate a coupling means membrane and a vessel membrane in order to establish an airtight connection between the injection agent container and the vessel.

4. The method according to claim 1, wherein the volume of the vessel changes, after the vessel is connected to the injection syringe, in order to achieve pressure equalization in the vessel as air is forced into the vessel and/or injection agent is withdrawn from the vessel.

5. The method according to claim 1, wherein a separate coupling means is attached to the connection nozzle such that during charging of the container with air, air passes through the air filter into the coupling means and from the coupling means through the connection nozzle into the container, whereafter the coupling means is connected to a vessel containing the injection agent.

* * * * *